US012359244B2

(12) United States Patent
Dean et al.

(10) Patent No.: US 12,359,244 B2
(45) Date of Patent: *Jul. 15, 2025

(54) RAPID EXTRACTION OF NUCLEIC ACIDS FROM CLINICAL SAMPLES FOR DOWNSTREAM APPLICATIONS

(71) Applicant: The Regents of the University of California, Oakland, CA (US)

(72) Inventors: Deborah Anne Dean, San Anselmo, CA (US); Noor Alnabelseya, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 1029 days.

This patent is subject to a terminal disclaimer.

(21) Appl. No.: 17/374,255

(22) Filed: Jul. 13, 2021

(65) Prior Publication Data

US 2022/0017945 A1 Jan. 20, 2022

Related U.S. Application Data

(63) Continuation of application No. 16/098,736, filed as application No. PCT/US2017/031138 on May 4, 2017, now Pat. No. 11,091,792.

(60) Provisional application No. 62/470,152, filed on Mar. 10, 2017, provisional application No. 62/331,881, filed on May 4, 2016.

(51) Int. Cl.
    *C12Q 1/68*     (2018.01)
    *C07H 1/06*     (2006.01)
    *C07H 21/00*    (2006.01)
    *C12Q 1/6806*   (2018.01)
    *C12Q 1/689*    (2018.01)

(52) U.S. Cl.
    CPC .......... *C12Q 1/6806* (2013.01); *C07H 1/06* (2013.01); *C07H 21/00* (2013.01); *C12Q 1/689* (2013.01)

(58) Field of Classification Search
    CPC ......... C12Q 1/68; C12Q 1/6806; C12N 15/10
    See application file for complete search history.

(56) References Cited

U.S. PATENT DOCUMENTS

| | | | |
|---|---|---|---|
| 4,755,356 A | 7/1988 | Robbin et al. | |
| 6,180,778 B1 | 1/2001 | Bastian et al. | |
| 7,264,941 B1 | 9/2007 | Birkelund et al. | |
| 8,691,969 B2 | 4/2014 | Deggerdal et al. | |
| 9,206,469 B2 | 12/2015 | Forman et al. | |
| 11,091,792 B2 * | 8/2021 | Dean ................. | C12N 15/1003 |
| 2005/0112631 A1 | 5/2005 | Piepenburg et al. | |
| 2005/0214926 A1 | 9/2005 | Zielenski et al. | |
| 2011/0015379 A1 | 1/2011 | Mori et al. | |
| 2011/0091883 A1 | 4/2011 | Ozsolak et al. | |
| 2011/0236891 A1 | 9/2011 | Li et al. | |
| 2011/0250648 A1 | 10/2011 | Manalili Wheeler et al. | |
| 2011/0251382 A1 * | 10/2011 | Deggerdal ........... | C12Q 1/6806 536/25.4 |
| 2012/0064511 A1 | 3/2012 | Leying Hermann et al. | |
| 2012/0115148 A1 | 5/2012 | Kawa et al. | |
| 2013/0017539 A1 | 1/2013 | Singhal et al. | |
| 2013/0022963 A1 | 1/2013 | Exner et al. | |
| 2014/0073988 A1 | 3/2014 | McSherry | |
| 2014/0199689 A1 | 7/2014 | Voss | |
| 2014/0212868 A1 | 7/2014 | Wilmes et al. | |
| 2014/0256929 A1 | 9/2014 | Loes et al. | |
| 2015/0086987 A1 | 3/2015 | Wolff et al. | |
| 2015/0337362 A1 * | 11/2015 | Tarendeau ........... | C12Q 1/6806 435/6.12 |
| 2015/0354005 A1 | 12/2015 | Mas Herrero et al. | |
| 2015/0368725 A1 | 12/2015 | Ho et al. | |
| 2016/0348189 A1 | 12/2016 | Schoenfeld | |
| 2016/0362729 A1 * | 12/2016 | Regan .................. | C12Q 1/6827 |

FOREIGN PATENT DOCUMENTS

EP          0981372         3/2000

OTHER PUBLICATIONS

Ahern, (1995) "Biochemical, Reagents Kits Offer Scientists Good Return on Investment", The Scientist, vol. 9, No. 15, p. 2 (7 pages).
Amer et al., (2013) "A new approach for diagnosis of bovine coronavirus using a reverse transcription recombinase polymerase amplification assay", Journal of Virological Methods, vol. 193, pp. 337-340.
Boyle et al., (2013) "Rapid Detection of HIV-1 Proviral DNA for Early Infant Diagnosis Using Recombinase Polymerase Amplification", vol. 4, No. 2, e00135-13, 8 pages.
Cetus, (1988) "GeneAmp DNA amplification Reagent Kit", 2 pages.
DTT (Dithiothreitol), Cell Signaling Technology dated Feb. 17, 2016, 1 page.
Farrell, (1999) "Evaluation of AMPLICOR Neisseria gonorrhoeae PCR Using cppB Nested PCR and 16S rRNA PCR", Journal of Clinical Microbiology, vol. 37, No. 2, pp. 386-390.
Hackstadt et al., (1985) "Disulfide-Mediated Interactions of the Chlamydial Major Outer Membrane Protein: Role in the Differentiation of Chlamydiae?", Journal of Bacteriology, vol. 161, No. 1, pp. 25-31.
Madico et al., (2000) "Touchdown Enzyme Time Release-PCR for Detection and Identification of Chlamydia trachomatis, C. pneumoniae, and C. psittaci Using the 16S and 16S-23S Spacer rRNA Genes", Journal of Clinical Microbiology, vol. 38, No. 3, pp. 1085-1093.

(Continued)

*Primary Examiner* — Ethan C Whisenant
(74) *Attorney, Agent, or Firm* — Shweta Chandra; Bozicevic, Field & Francis LLP

(57) ABSTRACT

Disclosed herein are novel methods and compositions for rapidly extracting and amplifying nucleic acids from a sample where the sample is combined with an extraction reagent comprising a reducing agent to form a mixture and incubating said mixture at ambient temperature for a period of time not exceeding 30 minutes to generate a nucleic acid extract. In certain embodiments of the method, the nucleic acid extract is subjected to a nucleic acid amplification reaction. In certain aspects, oligonucleotide primers specific for nucleic acids of *Chlamydia* species and/or *Neisseria* species are added prior to initiating the amplification reaction.

19 Claims, No Drawings

Specification includes a Sequence Listing.

(56) References Cited

OTHER PUBLICATIONS

PCT International Preliminary Report & Written Opinion for International Application No. PCT/US2017/031138, Jul. 26, 2017, 14 pages.
PCT International Preliminary Report on Patentability, PCT Application No. PCT/US2017/031138, Nov. 15, 2018, 7 pages.

* cited by examiner

RAPID EXTRACTION OF NUCLEIC ACIDS FROM CLINICAL SAMPLES FOR DOWNSTREAM APPLICATIONS

CROSS-REFERENCE TO RELATED APPLICATIONS

This application claims the benefit of U.S. Provisional Application Nos. 62/331,881, filed May 4, 2016, and 62/470,152, filed Mar. 10, 2017, which are hereby incorporated in their entirety by reference.

STATEMENT REGARDING FEDERALLY SPONSORED RESEARCH OR DEVELOPMENT

This invention was made with government support under grant number R01AI059647 awarded by the National Institutes of Health (NIH). The government has certain rights in the invention.

SEQUENCE LISTING

The instant application contains a Sequence Listing which has been submitted via EFS-Web and is hereby incorporated by reference in its entirety. Said ASCII copy, created on May 4, 2017, is named 37009PCT_CRF_sequencelisting.txt, and is 5,735 bytes in size.

BACKGROUND

Nucleic acid amplification based diagnostic assays for pathogenic infections such as *Chlamydia trachomatis* are more sensitive and accurate than enzyme immunoassay diagnostic assays (Watson et al.). However, current methods for diagnosing pathogenic infections that require nucleic acid extraction and amplification for the detection of the nucleic acids of the pathogen require performing a time consuming nucleic acid purification procedure with a plurality of steps prior to amplification of the nucleic acids. Similarly, current amplification based methods for diagnosing infections such as *Chlamydia trachomatis* or *Neisseria gonorrhoeae* are complicated, require a trained user and expensive equipment and supplies, take longer to perform and require a nucleic acid purification procedure prior to amplification of the nucleic acids. Therefore, there is great medical need for reliable, rapid diagnostic tests that allow nucleic acid amplification without the need for nucleic acid purification for diagnostic purposes.

SUMMARY OF THE INVENTION

Disclosed herein are novel methods for preparing a nucleic acid extract from a sample, the method comprising, obtaining the sample; combining the sample with an extraction reagent, the reagent comprising a reducing agent, and optionally a buffer, to form a mixture; sealing the mixture within a reaction vessel; and incubating the mixture in the sealed reaction vessel at ambient temperature for a period of time not exceeding 30 minutes to generate a nucleic acid extract.

In an aspect, the reducing agent is selected from the group consisting of dithiothreitol (DTT) and beta mercapto-ethanol (β-ME). In an aspect, the reducing agent is present at a concentration less than or equal to 40 mM.

In an aspect, the extraction reagent comprises a buffer. In an aspect, the buffer capacity of the mixture is less than or equal to 50 mM Tris at pH 8.5. In certain aspects, the buffer comprises less than or equal to 300 mM NaCl with 1.6 mM Tris. In an aspect, the buffer comprises DTT and the concentration of the DTT in the mixture is 1 mM to 40 mM. In an aspect, the concentration of the Tris in the mixture is 1.6 mM.

In an aspect, the ambient temperature ranges from 15° C. to 32° C.

In certain aspects, the period of time does not exceed 30 minutes. In certain aspects, the period of time does not exceed 20 minutes. In certain aspects, the period of time does not exceed 10 minutes. In certain aspects, the period of time does not exceed 5 minutes.

In an aspect, the sample is suspected of comprising bacteria. In an aspect, the bacteria comprise cysteine-rich cell walls. In certain aspects, the bacteria are selected from the group consisting of all *Chlamydia* species and strains, and all *Neisseria* species and strains. In certain aspects, the bacteria are selected from the group consisting of all *Chlamydia* species and strains.

In an aspect, the mixture is suitable for use in a nucleic acid amplification reaction. In an aspect, the methods comprise combining the mixture with a nucleic acid amplification reagent under conditions that promote a nucleic acid amplification reaction. In certain aspects, the amplification reaction is initiated not longer than 10 minutes following the conclusion of the incubation step. In certain aspects, the amplification reaction is initiated not longer than 5 minutes following the conclusion of the incubation step. In certain aspects, the amplification reaction is initiated not longer than 2 minutes following the conclusion of the incubation step.

In certain aspects, the nucleic acid amplification reaction is selected from the group consisting of a polymerase chain reaction, a loop mediated isothermal amplification, a strand displacement amplification, a multiple displacement amplification, a recombinase polymerase amplification, a helicase dependent amplification and a rolling circle amplification. In certain aspects, the nucleic acid amplification reaction is isothermal. In certain aspects, the nucleic acid amplification reaction is a loop-mediated isothermal amplification reaction.

In certain aspects, the nucleic acid amplification reagent comprises at least one or more primer pairs specific for *Chlamydia* species DNA genomic regions, *Neisseria* species DNA genomic regions, *Chlamydia* species RNA, *Neisseria* species RNA, or *Chlamydia* species plasmid regions, or combinations thereof. In certain aspects, a primer, comprising at least one or more primer pairs, comprises at least 15 contiguous nucleotides complementary to SEQ ID NOs: 1, 2, 3 or 4. In certain aspects, the nucleic acid amplification reagent comprises at least one or more primer pairs specific for a plurality of Lymphogranuloma venereum strains of *Chlamydia trachonatis*. In certain aspects, a primer, comprising at least one or more primer pairs, comprises at least 15 contiguous nucleotides complementary to SEQ ID NOs: 5 or 6. In certain aspects, the nucleic acid amplification reagent comprises at least one or more primer pairs specific for all strains of *Chlamydia* species or *Neisseria* species. In certain aspects, the nucleic acid amplification reagent comprises at least one or more primer pairs specific for any strain of *Chlamydia* species or *Neisseria* species.

In certain aspects, the extraction reagent comprises a detergent. In certain aspects, the detergent is Tween 20. In certain aspects, the extraction reagent comprises a PCR enhancer. In certain aspects, the PCR enhancer is Betaine. In certain aspects, the PCR enhancer is trimethylglycine. In certain aspects, the extraction reagent comprises a magnesium salt. In certain aspects, the magnesium salt is Magnesium Sulfate.

In certain aspects, the sample is obtained by a heath care provider. In certain aspects, the sample is obtained by the patient. In an aspect, the sample is a self-collected vaginal swab. In certain aspects, the sample is selected from the group consisting of an endocervical swab, vaginal swab, urethral swab, rectal swab, pharyngeal swab, and conjunctival swab or from remnant transport media from any of these types of swab samples.

Included herein are kits for preparing nucleic acids from a sample for amplification, wherein the kit comprises: an extraction reagent and one or more primer pairs. In certain aspects, this application describes kits comprising a reducing agent and the extraction reagent is configured to prepare the nucleic acids at ambient temperature for amplification at various temperatures no longer than 30 minutes after combining the sample with the extraction reagent, one or more primer pairs and instructions for use. In certain aspects, the kit comprises an extraction reagent containing DTT powder or liquid and a buffered solution, instructions for combining at least a portion of the sample with at least a portion of the DTT and at least a portion of the buffered saline solution to form a mixture and instructions for initiating a nucleic acid amplification reaction on the mixture. In certain aspects, the instructions direct a user of the kit to combine the sample with the extraction reagent and incubate at ambient temperature for not longer than 30 minutes post combining. In certain aspects, the kit comprises one or more primer pairs specific for nucleic acids of a *Chlamydia* species genome, a *Neisseria* species genome, a *Chlamydia* species plasmid or combinations thereof, at least one primer pair specific for Lymphogranuloma venereum strains and instructions for amplifying at least a region of *Chlamydia* and/or *Neisseria* species nucleic acids obtained from the *Chlamydia* species genome, the *Neisseria* species genome, the *Chlamydia* species plasmid or combinations thereof.

DETAILED DESCRIPTION OF THE INVENTION

Advantages and Utility

Briefly, and as described in more detail below, described herein are methods for rapid extraction of nucleic acids from a sample at ambient temperatures without the need for nucleic acid purification prior to amplification of the nucleic acids. The current approach can be used with multiple primer pairs or sets that allow for the identification of specific pathogens and specific strains of pathogens.

Advantages of this approach are numerous. The methods allow for a clinician, health care provider or patient to perform a rapid diagnostic test for any infection without the need for long incubation times or the need for a separate nucleic acid purification step prior to nucleic acid amplification. The methods also allow for a clinician, health care provider or patient to prepare the mixture for nucleic acid amplification without transferring the sample from a collection tool, such as a cotton swab prior to mixing the sample with the DTT mixture. Transfer of the sample from the sample collection tool to the mixture containing DTT is performed with ease. The cotton swab or other collection tool holding the patient sample can be inserted directly into a single vial containing DTT and buffer. In addition, the mixture of sample and DTT can be incubated at room temperature, and may not require another device to incubate the mixture at another temperature other than room temperature.

The nucleic acid amplification step can be performed immediately after the step of incubation with DTT. Alternatively, the nucleic acid amplification can occur at a later point and the mixture stored for a defined amount of time. Nucleic acid amplification can be performed using a number of methods including, but not limited to, the polymerase chain reaction or loop-mediated isothermal amplification (LAMP). LAMP allows for DNA amplification at a single constant temperature and does not require a thermocycler to perform the amplification.

Following nucleic acid amplification, detection of the amplification product can be performed by a number of means commonly used in the art such as, photometry, determination of turbidity or detection of fluorescence using intercalating dyes or detection of visible color change using dyes, such as intercalating dyes. Nucleic acid amplification can be detected by determination of calcein fluorescence upon complex formation of calcein loaded with manganese with pyrophosphate, wherein the pyrophosphate is produced as a byproduct from the nucleic acid amplification reaction.

The invention can be used for the detection of bacterial or non-bacterial pathogens in a patient sample without the need for long incubations or nucleic acid purification steps additional to the mixture comprising DTT and buffer. Because more than one primer pair specific for different sequences of nucleic acids may be used, this invention is useful for the detection of particular strains of pathogens, multiple different pathogens or multiple regions of a single strain of pathogen for confirmatory testing, using a single reaction mixture or nucleic acid amplification step.

An exemplary embodiment of the method is performing nucleic acid amplification of genomic DNA, ribosomal RNA or plasmid regions of Lymphogranuloma venereum and non-Lymphogranuloma venereum strains of *Chlamydia trachomatis*. An advantage to the invention is that it allows a patient or clinician to obtain test results with much greater speed and ease than current tests for infections such as, *Chlamydia trachomatis* and *Neisseria gonorrhoeae*.

Definitions

Terms used in the claims and specification are defined as set forth below unless otherwise specified.

The term "sample" refers to biological material obtained by a human, or biological material from a non-human animal or cells that have been cultured or uncultured.

The term "patient" refers to a human or non-human animal that is in need of diagnostic testing of a pathogen, or is suspected to have a pathogenic infection.

The term "pathogen" refers to an agent that causes disease or illness. A pathogen can be a virus, bacterium, fungus, protozoan or multi-cellular eukaryotic parasite.

The term, "cysteine-rich cell walls" refers to cells walls that comprise proteins, wherein the proteins have more than 6 cysteine residues.

The term, "buffer capacity" refers to the efficiency of a buffer in resisting changes in pH.

The term, "nucleic acid" refers to any nucleic acid polymers comprising nucleotides, including, but not limited to: DNA, genomic DNA, mRNA, tRNA, rRNA, siRNA, regulating RNA, non-coding and coding RNA, DNA fragments and DNA plasmids.

The term, "nucleic acid amplification" refers to an enzymatic reaction that utilizes a polymerase enzyme and nucleotides to synthesize nucleic acids from a nucleic acid template (e.g., polymerase chain reaction, a loop mediated isothermal amplification, a strand displacement amplification, a multiple displacement amplification, a recombinase polymerase amplification, a helicase dependent amplification or a rolling circle amplification).

The term, "nucleic acid amplification reagent" includes any reagent need to perform a nucleic amplification reaction (e.g., oligonucleotide primers, polymerase, buffer optimal for amplification, salts, etc.)

The term, "loop-mediated isothermal amplification (LAMP)" refers to a single tube or holding container technique for the amplification of nucleic acids at a constant temperature.

A DNA polymerase with strand displacement activity can be used in LAMP. LAMP can also be combined with a reverse transcription step to allow the detection of RNA, such as, but not limited to, mRNA and ribosomal RNA (rRNA). LAMP can include a plurality of primer pairs specific for distinct regions of nucleic acids. LAMP can include a plurality of loop primers. Loop primers can hybridize to stem-loops. Detection of the amplified nucleic acids can be determined by photometry, by detection of visible color change using intercalating dyes, or by the turbidity caused by an increasing amount of magnesium pyrophosphate precipitate in solution as a byproduct of the amplification reaction.

The term, "PCR enhancer" refers to a substance that is added to nucleic acid amplification reactions that increase the specificity and/or yield of a nucleic acid amplification reaction. PCR enhancers include, but are not limited to: dimethyl sulfoxide (DMSO), Betaine, trimethylglycine, formamide, non-ionic detergents (e.g., Triton X-100, Tween 20, Nonidet P40), tetramethylammonium chloride (TMAC), 7-deaza-2'deoxyganosine, bovine serum albumin (BSA) and T4 gene 32 protein.

The term "nucleic acid purification" refers to any method that leads to the isolation of nucleic acids from other biological material found in a sample. Nucleic acid purification techniques can include, but are not limited to, phenol-chloroform extraction techniques, column or magnetic purification using solid phase silica (including but not limited to, silicon oxide and glass powder, alkylsilica, aluminum silicate or activated silica with —$NH_2$), ethanol precipitation or isopropanol precipitation.

The term "buffered saline solution" refers to 0.90% w/v of NaCl or 9.0 g per liter.

The term "primer" refers to oligonucleotides no more than 50 nucleotide bases in length, usually between 15 and 25 bases in length, that specifically bind to a nucleic acid sequence of interest for the purpose of performing a nucleic acid amplification reaction.

The term "primer set" refers to a pair of oligonucleotide primers that bind to opposite ends or boundaries of a target nucleic acid template sequence in opposite orientations for amplifying a desired region of the template.

The term "complementary" as used herein refers to a complement of the sequence by Watson-Crick base pairing, whereby guanine (G) pairs with cytosine (C), and adenine (A) pairs with either uracil (U) or thymine (T). A sequence can be complementary to the entire length of another sequence, or it can be complementary to a specified portion or length of another sequence. One of skill in the art will recognize that U can be present in RNA, and that T can be present in DNA. Therefore, an A within either of a RNA or DNA sequence can pair with a U in a RNA sequence or T in a DNA sequence. The term "complementary" is used to indicate a sufficient degree of complementarity or precise pairing such that stable and specific binding occurs between nucleic acid sequences e.g., between a primer sequence and the target sequence (e.g., nucleotide sequence) of interest. It is understood that the sequence of nucleic acids need not be 100% complementary to that of its target or complement. In some cases, the sequence is complementary to the other sequence with the exception of 1-2 mismatches. In some cases, the sequences are complementary except for 1 mismatch. In some cases, the sequences are complementary except for 2 mismatches. In other cases, the sequences are complementary except for 3 mismatches. In yet other cases, the sequences are complementary except for 4, 5, 6, 7, 8, 9 or more mismatches.

The term "swab" refers to a tool or device used for collecting a sample that comprises a handle or stick and a piece of cotton or Dacron or other material at one end that comes in contact with the sample and holds the sample upon collection.

The term "in vivo" refers to processes that occur in a living organism.

The term "mammal" as used herein includes both humans and non-humans and includes but is not limited to humans, non-human primates, canines, felines, murines, bovines, equines, caprines, caviines, mellivorines, arvicolines and porcines.

The term percent "identity," in the context of two or more nucleic acids or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nim.nih.gov/).

It must be noted that, as used in the specification and the appended claims, the singular forms "a," "an" and "the" include plural referents unless the context clearly dictates otherwise.

Methods of the Invention

In certain embodiments, the methods of the invention include resuspending DTT in ddH$_2$O and phosphate buffered saline in a container. A swab containing a sample suspected of comprising nucleic acids of interest is added to the DTT, Tris, H$_2$O and phosphate buffered saline mixture. In some embodiments the mixture can contain a salt, Tris, H$_2$O and phosphate buffered mixture. In some aspects, the sample can be any patient-derived fluid, secreted or excreted, or any patient-derived tissue. In an embodiment, the sample can be on a swab. In an embodiment, the sample is obtained by a health care provider. In another embodiment, the sample is obtained by the patients themselves. The DTT and sample are allowed to incubate in order to extract the nucleic acids from the sample. In certain aspects, the incubation takes less than 30 minutes, or less than 20, 15, 12, or 10 minutes. In an aspect, the incubation occurs at ambient temperature or room temperature. Following the incubation, the nucleic acids are removed from the container. In an embodiment, the nucleic acids are removed by using another sterile swab or thin elongated tool to lift the nucleic acids out of the container. In another embodiment, the nucleic acids are separated from the supernatant by centrifugation. In yet another embodiment, the nucleic acids are filtered from the supernatant.

The supernatant can be used for diagnostic applications. In an aspect, the diagnostic application comprises polymerase chain reaction nucleic acid amplification. The amplification step can be performed soon after the step of incubation with DTT. Alternatively, the nucleic acid amplification can occur at a later point and the mixture stored for an indefinite amount of time. Nucleic acid amplification can be performed using a number of methods including, but not limited to, the polymerase chain reaction or loop-mediated isothermal amplification (LAMP). LAMP allows for nucleic acid amplification at a single constant temperature and does not require a thermocycler to perform the amplification.

In an aspect of the method, one or more nucleic acid primers are added to a mixture comprising the supernatant. In certain aspects, the nucleic acid primers can be complementary to a genomic DNA region, a plasmid, a ribosomal RNA or an mRNA of the nucleic acids of interest. In an embodiment, the nucleic acid primers are complementary to the genomic nucleic acid sequence of a Lymphogranuloma venereum strain of *Chlamydia trachomatis*. In another embodiment, the nucleic acid primers are complementary to the genomic nucleic acid sequence non-Lymphogranuloma strains of *Chlamydia trachomatis*. In another embodiment, the primers are complementary to a plasmid DNA sequence containing a portion of the genomic DNA sequence of a Lymphogranuloma venereum strain of *Chlamydia trachomatis*. In yet another embodiment, the primers are complementary to a plasmid DNA sequence containing a portion of the genomic DNA sequence of a non-Lymphogranuloma venereum strain of *Chlamydia trachomatis*. In another embodiment, the primers are complementary to a ribosomal RNA sequence of a non-Lymphogranuloma venereum strain of *Chlamydia trachomatis*. In another embodiment, the primers are complementary to a ribosomal RNA sequence of a Lymphogranuloma venereum strain of *Chlamydia trachomatis*. In certain embodiments, the primers are complementary to a genomic DNA sequence or a ribosomal RNA sequence of *Neisseria gonorrhoeae*.

Following nucleic acid amplification, detection of the amplification product can be performed by photometry, determination of turbidity, or detection of fluorescence using intercalating dyes or detection of visible color change using intercalating dyes. Nucleic acid amplification can be detected by determination of calcein fluorescence upon complex formation of calcein loaded with manganese with pyrophosphate, wherein the pyrophosphate is produced as a byproduct from the nucleic acid amplification reaction.

In an embodiment, the method comprises agarose gel electrophoresis. In another embodiment, the method comprises use of a microarray. In yet another embodiment, the method comprises use of a microfluidic device. In an aspect, the method comprises a detection step. In an embodiment, the detection step requires a physical sensor. In yet another embodiment the detection step requires an electrical sensor. In yet another embodiment, the detection step results in the production of signals of different colors or signals of different intensities. In an embodiment, the detection step requires a separate detection device.

EXAMPLES

Below are examples of specific embodiments for carrying out the present invention.

The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* 3$^{rd}$ Ed. (Plenum Press) Vols A and B(1992).

Example 1: Protocol for Rapid Lysis of Clinical Samples and Preparation of Samples for qPCR Amplification Lysis of Samples:

Lysis buffer (pH>7) was prepared with a final concentration of 15 mM DTT and 1.6 mM Tris. Nuclease free ddH$_2$O was added to a total volume of 500 µL. 25 µL of clinical remnant sample or original clinical swab sample was then added to the lysis buffer followed by incubation of the sample in lysis buffer for 5 minutes at room temperature.

Amplification of Sample Nucleic Acids by Quantitative PCR:

14 µL of lysate was added to respective amplification master mix tube with 21 µL master mix (comprising primers, dNTP) giving a total volume of 35 µL for triplicate (3 wells with 10 µL each) and 10 µL per well into a 384 well plate.

4 µL of lysate was mixed with 6 µL master mix per amplification reaction. The plate was centrifuged for 30 seconds @1500 rpm, 4° C. For quantitative PCR, mastermix was prepared for each sample: 5 µL of SYBR® green PCR reaction mix, 0.5 µL (10 µm) of each primer and 4 µL of nuclease free water for a total of 10 µL per well. PCR amplification was performed on a Bio-Rad® CFX384 thermocycler for one hour with 5 minutes initial denaturation at 95° C. and 40 cycles of denaturation for 10 seconds at 95° C. followed by annealing/extension combined step for 30 seconds at 60° C.

Example 2: Detection of *Chlamydia trachomatis* Plasmid DNA by qPCR

Patient samples were prepared for quantitative PCR as described above in Example 1. Oligonucleotide primer pairs specific for *Chlamydia trachomatis* plasmid DNA were added to the mixture containing patient samples obtained from a clinician. Quantitative PCR DNA amplification was performed as described in Example 1 above. *Chlamydia trachomatis* plasmid DNA was detected in two out of 19 patient samples (Table 1, samples 2 and 19 denoted in grey below). Table 1 depicts the results for the above experiment.

TABLE 1

Detection of *Chlamydia trachomatis* plasmid DNA by qPCR in patient samples (values represent mean of triplicates)

| Sample | GAPDH Cq | *Chlamydia* Cq mean | Copies/µL |
|---|---|---|---|
| 1 | 24.69776 | 28.59696 | 5.352926 |
| 2 | 23.43752 | 24.1474 | 189.1244 |
| 3 | 32.99246 | 33.91647 | 0.075465 |
| 4 | 34.7881 | 32.87438 | 0.17391 |
| 5 | 34.91491 | 32.55277 | 0.225023 |
| 6 | 32.40667 | 33.13663 | 0.140955 |
| 7 | 33.29668 | 32.96674 | 0.161507 |
| 8 | 35.83426 | 31.56829 | 0.495177 |
| 9 | 32.62517 | 32.36708 | 0.261116 |
| 10 | 32.86848 | 33.33336 | 0.120401 |
| 11 | 25.2408 | 29.02308 | 3.804773 |
| 12 | 30.85988 | 35.71968 | 0.017797 |
| 13 | 32.9791 | 31.65934 | 0.460343 |
| 14 | 32.95388 | 33.36076 | 0.117787 |
| 15 | 32.16459 | 31.98019 | 0.355998 |
| 16 | 30.92737 | 31.52933 | 0.510877 |
| 17 | 30.56799 | 32.389 | 0.256571 |
| 18 | 29.91723 | 32.30879 | 0.273598 |
| 19 | 32.8704 | 22.46343 | 728.8837 |
| Water | N/A | 34.02144 | 0.069378 |
| Standard 1 | N/A | 13.098160 | $10^{\wedge}6$ |
| Standard 2 | N/A | 16.424252 | $10^{\wedge}5$ |
| Standard 3 | N/A | 19.359287 | $10^{\wedge}4$ |
| Standard 4 | N/A | 22.755613 | $10^{\wedge}3$ |
| Standard 5 | N/A | 24.399755 | $10^{\wedge}2$ |
| Standard 6 | N/A | 27.752134 | $10^{\wedge}1$ |

Example 2: Detection of *Chlamydia trachomatis* *Chlamydia trachomatis* Plasmid DNA by LAMP Patient samples were lysed and prepared for LAMP assay as described above in Example 1. A master mixture for LAMP amplification was prepared with a final concentration of 1.4 mM dNTPs, 0.48 M Betaine (Sigma® catalog #B0300-1VL), 0.06% Tween 20, 1× primer set specific for *Chlamydia trachomatis* plasmid DNA, 0.6× salt mix, 1× EvaGreen®, 8 U of BST 2.0 Enzyme (New England Bio-Labs, catalog #M0537L), 3.75 U reverse transcriptase and 5 U RNase inhibitor (Thermo Fisher/Applied Biosystems catalog, #N8080119). 14 µL of lysed sample was added to 21 µL of master mix for each sample to generate the reaction mixture (to perform the reaction in triplicate in 3 wells per sample). 10 µL of reaction mixture (comprising 4 µL of lysate and 6 µl of mater mix per reaction) was added to each well on a 384 well plate. DNA amplification was performed on a Bio-Rad® CFX384 thermocycler for 1 hour at 63° C. Results are shown in Table 2 for detection of *Chlamydia trachomatis* plasmid DNA. Patient samples 13 and 15 were positive (Table 2, denoted in grey) and consistent with the standards while negative controls (water and lysis buffer) were negative. Note that each sample was run in triplicate and the Cq value represents the mean.

TABLE 2

Detection of *Chlamydia trachomatis* plasmid DNA by LAMP in patient samples (values represent mean of triplicates).

| Sample | *Chlatnydia* Cq mean |
|---|---|
| 1 | 35.23 |
| 2 | 36.70 |
| 3 | 36.46 |
| 4 | 35.30 |
| 5 | 36.04 |
| 6 | 37.28 |
| 7 | 36.16 |
| 8 | 32.96 |
| 9 | 35.28 |
| 10 | 34.25 |
| 11 | 33.07 |
| 12 | 33.72 |
| 13 | 30.32 |
| 14 | 33.07 |
| 15 | 29.79 |
| Lysis buffer alone | 0.0 |
| Water | 0.0 |
| Standard 1-$10^{\wedge}6$ | 14.48 |
| Standard 2-$10^{\wedge}5$ | 17.98 |
| Standard 3-$10^{\wedge}4$ | 70.56 |
| Standard 4-$10^{\wedge}3$ | 25.31 |
| Standard 5-$10^{\wedge}2$ | 27.38 |
| Standard 6-$10^{\wedge}1$ | 30.94 |

Example 3: Detection of *Neisseria gonorrhoeae* Ribosomal RNA by qPCR

Patient samples were prepared for quantitative PCR as described above in Example 1. Oligonucleotide primer pairs specific for *Neisseria gonorrhoeae* 16S ribosomal RNA were added to the mixture containing patient samples obtained from a clinician. Quantitative PCR amplification was performed as described in Example 1 above. Results are shown in Table 3 below. All samples were positive for *Neisseria gonorrhoeae* denoted in grey (Table 3).

TABLE 3

Detection of *Neisseria gonorrhoeae* 16S ribosomal RNA by qPCR in patientsamples (values represent mean of triplicates)

| Sample | 16S rRNA Cq | Copies/µL |
|---|---|---|
| 1 | 19.74 | 1.83E+05 |
| 2 | 23.93 | 1.33E+04 |
| 3 | 33.73 | 2.90E+01 |
| 4 | 27.99 | 1.05E+03 |
| 5 | 30.96 | 1.64E+02 |
| 6 | 16.37 | 1.51E+06 |
| Lysis buffer alone | 0.00 | 0.00E+00 |
| Standard 1 | 16.99 | $10^{\wedge}6$ |
| Standard 2 | 20.46 | $10^{\wedge}5$ |
| Standard 3 | 25.07 | $10^{\wedge}4$ |

TABLE 3-continued

Detection of Neisseria gonorrhoeae 16S ribosomal RNA by qPCR in patientsamples (values represent mean of triplicates)

| Sample | 16S rRNA Cq | Copies/µL |
|---|---|---|
| Standard 4 | 26.89 | $10^3$ |
| Standard 5 | 33.28 | $10^2$ |
| Standard 6 | 34.71 | $10^1$ |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

Watson E. J., et al., The accuracy and efficacy of screening tests for *Chlamydia trachomatis*: a systemic review.; J. Med. Microbiol. Dec. 5, 2002 (12): 1021-31.

The invention claimed is:

1. A method comprising:
   incubating a mixture comprising (i) a sample suspected of comprising bacteria and (ii) an extraction reagent at ambient temperature for a period of time not exceeding 30 minutes to generate a nucleic acid extract,
   wherein the reagent comprises a reducing agent, and optionally a buffer; and
   combining the mixture comprising the nucleic acid extract with a nucleic acid amplification reagent under conditions that promote nucleic acid amplification of the nucleic acid extract.

2. The method of claim 1, wherein the reducing agent is dithiothreitol (DTT).

3. The method of claim 2, wherein the DTT is present at a concentration of 1 mM to 40 mM.

4. The method of claim 1, wherein the reducing agent is beta mercapto-ethanol (β-ME).

5. The method of claim 4, wherein the β-ME is present at a concentration less than or equal to 40 mM.

6. The method of claim 1, wherein the extraction reagent comprises a buffer, and wherein the buffer provides a buffering capacity within the mixture that is less than a buffering capacity of 50 mM Tris at pH8.5.

7. The method of claim 1, wherein the extraction reagent comprises a buffer comprising Tris at a concentration of 1.6 mM.

8. The method of claim 1, wherein the ambient temperature ranges from 15° C. to 32° C. and the period of time does not exceed 20 minutes or 10 minutes.

9. The method of claim 1, wherein the ambient temperature ranges from 15° C. to 32° C. and the period of time does not exceed 2 minutes or 5 minutes.

10. The method of claim 1, wherein the bacteria comprise cysteine-rich cell walls.

11. The method of claim 1, wherein the bacteria are selected from the group consisting of all *Chlamydia* species and strains and all *Neisseria* species and strains.

12. The method of claim 1, wherein the nucleic acid amplification is initiated not later than 10 minutes following the conclusion of the incubation step.

13. The method of claim 1, wherein the nucleic acid amplification is initiated not later than 5 minutes or no later than 2 minutes following the conclusion of the incubation step.

14. The method of claim 1, wherein the nucleic acid amplification occurs via a reaction selected from the group consisting of a polymerase chain reaction (PCR), a loop-mediated isothermal amplification (LAMP), a strand displacement amplification, a multiple displacement amplification, a recombinase polymerase amplification, a helicase dependent amplification and a rolling circle amplification.

15. The method of claim 1, wherein the nucleic acid amplification occurs via an isothermal reaction.

16. The method of claim 1, wherein the extraction reagent comprises a detergent.

17. The method of claim 1, wherein the extraction reagent comprises a PCR enhancer, wherein the PCR enhancer is betaine or trimethylglycine.

18. The method of claim 1, wherein the extraction reagent comprises a magnesium salt.

19. The method of claim 1, wherein the sample is selected from the group consisting of an endocervical swab, vaginal swab, urethral swab, pharyngeal swab, conjunctival swab and rectal swab or from remnant transport media from any of these types of swab samples.

* * * * *

SEQUENCE LISTING

<160> NUMBER OF SEQ ID NOS: 6

<210> SEQ ID NO 1
<211> LENGTH: 585
<212> TYPE: DNA
<213> ORGANISM: Chlamydia trachomatis

<400> SEQUENCE: 1

```
actcctagtt gaacacatct ggaaagatgg atgatacagg gtgatagtcc cgtagacgaa      60
aggagagaaa gaccgacctc aacacctgag taggactaga cacgtgaaac ctagtctgaa     120
tctggggaga ccactctcca aggctaaata ctagtcaatg accgatagtg aaccagtact     180
gtgaaggaaa ggcgaaaaga acccttgtta agggagtgaa atagaacctg aaaccagtag     240
cttacaagcg gtcggagacc aatggcccgt aagggtcaag gttgacggcg tgcctttgc     300 atgatgagcc agggagttaa gctaaacggc gaggttaagg gatatacatt ccggagccgg     360
agcgaaagcg agttttaaaa gagcgaagag tcgtttggtt tagacacgaa accaagtgag     420
ctatttatga ccaggttgaa gcatgggtaa aactatgtgg aggaccgaac tagtacctgt     480
tgaaaaaggt ttggatgagt tgtgaatagg ggtgaaaggc caatcaaact tggagatatc     540
ttgttctctc cgaaataact ttagggttag cctcggataa taagc                     585
```

<210> SEQ ID NO 2
<211> LENGTH: 559
<212> TYPE: DNA
<213> ORGANISM: Chlamydia trachomatis

<400> SEQUENCE: 2

```
ttatccccgt aacttcggaa taaggggagc cttttagggt gactatggaa cgataggagc      60 cccgggggc cgcagagaaa tggcccaggc gactgtttag caaaaacaca gcactatgca     120
aacctctaag gggaagtata tggtgtgacg cctgcccaat gccaaaaggt taaagggata     180
tgtcagctgc aaagtgaagc attgaaccta agccctggtg aatggccgcc gtaactataa     240
cggtgctaag gtagcgaaat tccttgtcgg gtaagttccg acctgcacga atggtgtaac     300
gatctgggca ctgtctcaac gaaagactcg gtgaaattgt agtagcagtg aagatgctgt     360 ttaccgcga aaggacgaaa agaccccgtg aacctttact gtactttggt attgattttt      420
ggtttgttat gtgtaggata gccaggagac taagaacact cttcttcagg agagtgggag     480
tcaacgttga aatactggtc ttaacaagct gggaatctaa cattattcca tgaatctgga     540
agatggacat tgccagacg                                                   559
```

<210> SEQ ID NO 3
<211> LENGTH: 500
<212> TYPE: DNA

<213> ORGANISM: Chlamydia trachomatis

<400> SEQUENCE: 3

```
gaatttgatc ttggttcaga ttgaacgctg gcggcgtgga tgaggcatgc aagtcgaacg      60
gagcaattgt ttcgacgatt gtttagtggc ggaagggtta gtaatg <213> ORGANISM: Artificial Sequence
<220> FEATURE:
<223> OTHER INFORMATION: Description of Artificial Sequence: Synthetic
      polynucleotide

<400> SEQUENCE: 6

```
atcaaataga atcctacttt gtaatcaagc ctgcaaatgt ataccaagaa ataaaaatgc      60
gcttcccaaa tgcatcaaag tatgcttaca catttatcga ctgggtgatt acagcagctg     120
cgaaaaagag acgaaaatta actaaggata attcttggcc agaaaacttg ttcttaaacg     180
ttaacgttaa aagtcttgca tatattttaa ggatgaatcg gtacatttgt acaaggaact     240
ggaaaaaaat cgagttagct atcgataaat gtatagaaat cgccattcag attggttggt     300
tatctagaag aaaacgcatt gaatttctgg attcttctaa actctctaaa aaagaaattc     360
tatatctaaa taaagagcgt tttgaagaaa taactaagaa atctaaagaa caaatggaac     420
aattagaaca agaatctatt aattaatagc aaacttgaaa ctaaaaacct aatttattta     480
aagctcaaaa taaaaagag ttttaaaatg ggaaattctg gtttttattt gtataacact     540
```

```
caaaactgcg tctttgctga taatatcaaa gttgggcaaa tgacagagcc gctcaaggac     600
agcaaataat ccttgggaca acatcaacac ctgtcgcagc caaaatgaca gcttctgatg     660
gaatatcttt aacagtctcc aataatccat caaccaatgc ttctattaca attggtttgg     720
atgcggaaaa agcttaccag cttattctag aaaagttggg agatcaaatt cttggtggac     780
cttctctagg tttgttgaaa gcttttaaca actttccaat cactaataaa attcaatgca     840
acgggttatt cactcccagg aacattgaaa ctttattagg aggaactgaa ataggaaaa      899
```